US008348988B2

(12) United States Patent
Lad et al.

(10) Patent No.: US 8,348,988 B2
(45) Date of Patent: Jan. 8, 2013

(54) ENDOLUMINAL PROSTHETIC DEVICE (75) Inventors: Ashvin Lad, Indianapolis, IN (US); Michael P. DeBruyne, Bloomington, IN (US); Thomas A. Osborne, Bloomington, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 778 days.

(21) Appl. No.: 11/037,792

(22) Filed: Jan. 18, 2005

(65) Prior Publication Data

US 2005/0159803 A1 Jul. 21, 2005

Related U.S. Application Data (60) Provisional application No. 60/537,980, filed on Jan. 20, 2004.

(51) Int. Cl.
*A61F 2/06* (2006.01)
(52) U.S. Cl. ..................................... 623/1.13
(58) Field of Classification Search ................ 623/1.11, 623/1.13, 1.14, 1.16, 1.44, 1.23, 1.32, 1.33, 623/1.36
See application file for complete search history.

(56) References Cited

U.S. PATENT DOCUMENTS

| 4,306,562 | A | 12/1981 | Osborne |
|---|---|---|---|
| 4,405,314 | A | 9/1983 | Cope |
| 4,430,081 | A | 2/1984 | Timmermans |
| 4,445,896 | A | 5/1984 | Gianturco |
| 4,494,531 | A | 1/1985 | Gianturco |
| 4,548,206 | A | 10/1985 | Osborne |
| 4,551,137 | A | 11/1985 | Osborne |
| 4,580,568 | A | 4/1986 | Gianturco |
| 4,800,882 | A | 1/1989 | Gianturco |
| 4,907,336 | A | 3/1990 | Gianturco |
| 5,037,377 | A | 8/1991 | Alonso |
| 5,041,126 | A | 8/1991 | Gianturco |
| 5,282,824 | A | 2/1994 | Gianturco |

(Continued)

FOREIGN PATENT DOCUMENTS

EP 0 508 473 A2 10/1992

(Continued)

OTHER PUBLICATIONS

International Search Report dated Jun. 26, 2005 for PCT Application No. PCT/US2005/001830.

(Continued)

*Primary Examiner* — Tuan V Nguyen
*Assistant Examiner* — Thomas McEvoy
(74) *Attorney, Agent, or Firm* — Brinks Hofer Gilson & Lione (57) ABSTRACT

An endoluminal prosthetic device for placement in a body lumen is formed by stitching stents to a graft. A first or anchoring stent is used for securing a graft made of biocompatible material that forms at least one lumen. There is also a second stent. The first and second stents each include a plurality of struts and apices between the struts. At least two of the apices in each of the first and second stents are secured to the graft by stitches. A running suture links at least one stitch of the first stent and one stitch of the second stent. The running suture linking the first stent and the second stent adds strength to the stitches and better secures the first stent to the device. The endoluminal prosthetic device may be used in an aortic vessel to treat stenoses or aneurysms.

20 Claims, 6 Drawing Sheets

U.S. PATENT DOCUMENTS

| | | | | |
|---|---|---|---|---|
| 5,314,444 | A | 5/1994 | Gianturco | |
| 5,314,472 | A | 5/1994 | Fontaine | |
| 5,342,371 | A | 8/1994 | Welter et al. | |
| 5,443,498 | A | 8/1995 | Fontaine | |
| 5,456,713 | A | 10/1995 | Chuter | |
| 5,507,771 | A | 4/1996 | Gianturco | |
| 5,527,354 | A | 6/1996 | Fontaine et al. | |
| 5,562,697 | A | 10/1996 | Christiansen | |
| 5,562,724 | A | 10/1996 | Vorwerk et al. | |
| 5,562,726 | A | 10/1996 | Chuter | |
| 5,562,728 | A | 10/1996 | Lazarus et al. | |
| 5,632,771 | A | 5/1997 | Boatman et al. | |
| 5,643,339 | A | 7/1997 | Kavteladze et al. | |
| 5,683,451 | A | 11/1997 | Lenker et al. | |
| 5,720,776 | A | 2/1998 | Chuter et al. | |
| 5,733,325 | A | 3/1998 | Robinson et al. | |
| 5,755,777 | A | 5/1998 | Chuter | |
| 5,824,037 | A * | 10/1998 | Fogarty et al. | 623/1.13 |
| 5,824,044 | A | 10/1998 | Quiachon et al. | |
| 5,897,589 | A | 4/1999 | Cottenceau et al. | |
| 5,935,161 | A | 8/1999 | Robinson et al. | |
| 6,004,347 | A | 12/1999 | McNamara et al. | 623/1 |
| 6,015,431 | A | 1/2000 | Thornton et al. | 623/1 |
| 6,024,763 | A | 2/2000 | Lenker et al. | |
| 6,077,296 | A | 6/2000 | Shokoohi et al. | |
| 6,077,297 | A | 6/2000 | Robinson et al. | 623/1.11 |
| 6,176,875 | B1 | 1/2001 | Lenker et al. | |
| 6,193,745 | B1 | 2/2001 | Fogarty et al. | |
| 6,200,336 | B1 | 3/2001 | Pavcnik et al. | |
| 6,221,102 | B1 | 4/2001 | Baker et al. | 623/1.36 |
| 6,231,598 | B1 | 5/2001 | Berry et al. | |
| 6,287,330 | B1 | 9/2001 | Johansson et al. | 623/1.13 |
| 6,312,458 | B1 * | 11/2001 | Golds | 623/1.13 |
| 6,325,819 | B1 | 12/2001 | Pavcnik et al. | |
| 6,524,336 | B1 | 2/2003 | Papazolgou et al. | |
| 6,660,033 | B1 * | 12/2003 | Marcade et al. | 623/1.16 |
| 6,899,728 | B1 | 5/2005 | Phillips et al. | |
| 6,951,572 | B1 * | 10/2005 | Douglas | 623/1.35 |
| 7,147,660 | B2 | 12/2006 | Chobotov et al. | 623/1.14 |
| 7,175,652 | B2 | 2/2007 | Cook et al. | |
| 7,238,198 | B2 | 7/2007 | Hartley et al. | |
| 2001/0041928 | A1 * | 11/2001 | Pavcnik et al. | 623/1.13 |
| 2003/0088305 | A1 | 5/2003 | Van Schie et al. | |
| 2003/0176911 | A1 | 9/2003 | Iancea et al. | |
| 2003/0176912 | A1 * | 9/2003 | Chuter et al. | 623/1.13 |
| 2004/0049262 | A1 | 3/2004 | Obermiller et al. | 623/1.15 |
| 2005/0159803 | A1 | 7/2005 | Lad et al. | 623/1.13 |
| 2005/0159804 | A1 | 7/2005 | Lad et al. | 623/1.13 |
| 2009/0299462 | A1 | 12/2009 | Fawzi et al. | |

FOREIGN PATENT DOCUMENTS

| | | |
|---|---|---|
| EP | 1 029 517 A2 | 8/2000 |
| EP | 1 706 069 B1 | 10/2006 |
| EP | 1 706 070 B1 | 2/2011 |
| JP | 4887159 B2 | 7/2007 |
| JP | 4970053 B2 | 7/2007 |
| JP | 2007518532 A | 7/2007 |
| JP | 2007518538 A | 7/2007 |
| JP | 2011-218230 A | 11/2011 |
| WO | WO 96/39999 | 12/1996 |
| WO | WO 00/61034 A | 10/2000 |
| WO | WO 03/075799 A1 | 9/2003 |
| WO | WO 2004/002365 A1 | 1/2004 |
| WO | WO 2005/070337 A2 | 8/2005 |
| WO | WO 2005/070337 A3 | 8/2005 |
| WO | WO 2005/070338 A1 | 8/2005 |

OTHER PUBLICATIONS

International Search Report, dated Dec. 7, 2005, for PCT Application No. PCT/US2005/002108.

Prosecution History for U.S. Appl. No. 11/038,567, Osborne et al., filed Jan. 18, 2005.

* cited by examiner

FIG. 10

ENDOLUMINAL PROSTHETIC DEVICE

This application claims the benefit of the filing date under 35 U.S.C. §119(e) of Provisional U.S. patent application Ser. No. 60/537,980, filed on Jan. 20, 2004, which is hereby incorporated by reference in its entirety.

FIELD OF THE INVENTION

The field of the invention is that of stents and the attachment of stents to grafts useful for insertion into a body passageway, and in particular stents and grafts for use in a vascular passageway.

BACKGROUND

Stent-grafts are used in body lumens and in particular, in vascular lumens. These grafts allow the use of the lumen in situations where the lumen may have a defect, such as a stenosis or an aneurysm. Stents perform functions that make them useful in combination with grafts. External stents are used to pull grafts open while avoiding the use of metallic materials on the inside of a graft, where the metals would be in contact with body fluids, such as blood. External stents thus avoid placement where they would be in contact with the body fluid. External stents, outside the graft, also avoid interference with the flow of the body fluid and are not an obstacle to passage of other medical devices though the inside of the graft. Internal stents are used to push the grafts open and to help seal the graft against the vessel wall. A stent, such as a zigzag stent, also may be used to anchor a graft in place, provided there are anchors or barbs on the stent for securing the stent, and hence the graft, in the desired location.

Previous grafts have included stents, but sometimes have defects that hinder their use. For example, FIG. 2 of U.S. Pat. No. 6,004,347 depicts a stent that may be difficult to manufacture because of the many resistance welds. A more serious difficulty is the method used to attach the stent to the graft. In order to properly secure the stent to the graft, according to the patent, eight penetrations or holes are needed for four successive stitches. Each stitch is positioned further away from a bend in the proximal end of the stent. This method spreads out the stress on the graft from the stent, but requires many penetrations per bend of the stent.

FIGS. 17-18 of U.S. Pat. No. 6,287,330 and FIGS. 19-21 of U.S. Pat. No. 6,221,102 depict stents used to secure a graft material. In these examples, the stent is separate from an attachment system that anchors the graft to the body lumen. Many stitches are required to secure the stent and the attachment system to the graft.

BRIEF SUMMARY

One aspect of the invention is an endoluminal prosthetic device, comprising a graft comprising a bio-compatible material forming at least one lumen, a first stent comprising a plurality of struts and apices between the struts, at least two of the apices in the first stent secured to the graft by stitches. The endoluminal prosthetic device also comprises a second stent comprising a plurality of struts and apices between the struts, at least two of the apices secured to the graft by stitches, wherein at least one stitch of the first stent and at least one stitch of the second stent are joined in a running suture.

Another aspect of the invention is a method of forming an endoluminal prosthetic device, the method comprising providing a graft, and joining a first stent to the graft, the first stent comprising a plurality of struts and apices between the struts, by at least a stitch on each apex. The method also comprises joining a second stent to the graft, the second stent comprising a plurality of struts and apices between the struts, by at least a stitch on each apex, and linking at least one stitch of the first stent and one stitch of the second stent with a running suture. There are many ways to practice the present invention, as shown in the following drawings and specification. The embodiments are not meant to limit the invention, but rather to describe and illustrate some of the ways that the present invention may be used.

BRIEF DESCRIPTION OF THE DRAWINGS

FIG. 5b is a closer view of FIG. 5a.

DETAILED DESCRIPTION OF THE PREFERRED EMBODIMENTS

Figures 1, 2, 3:
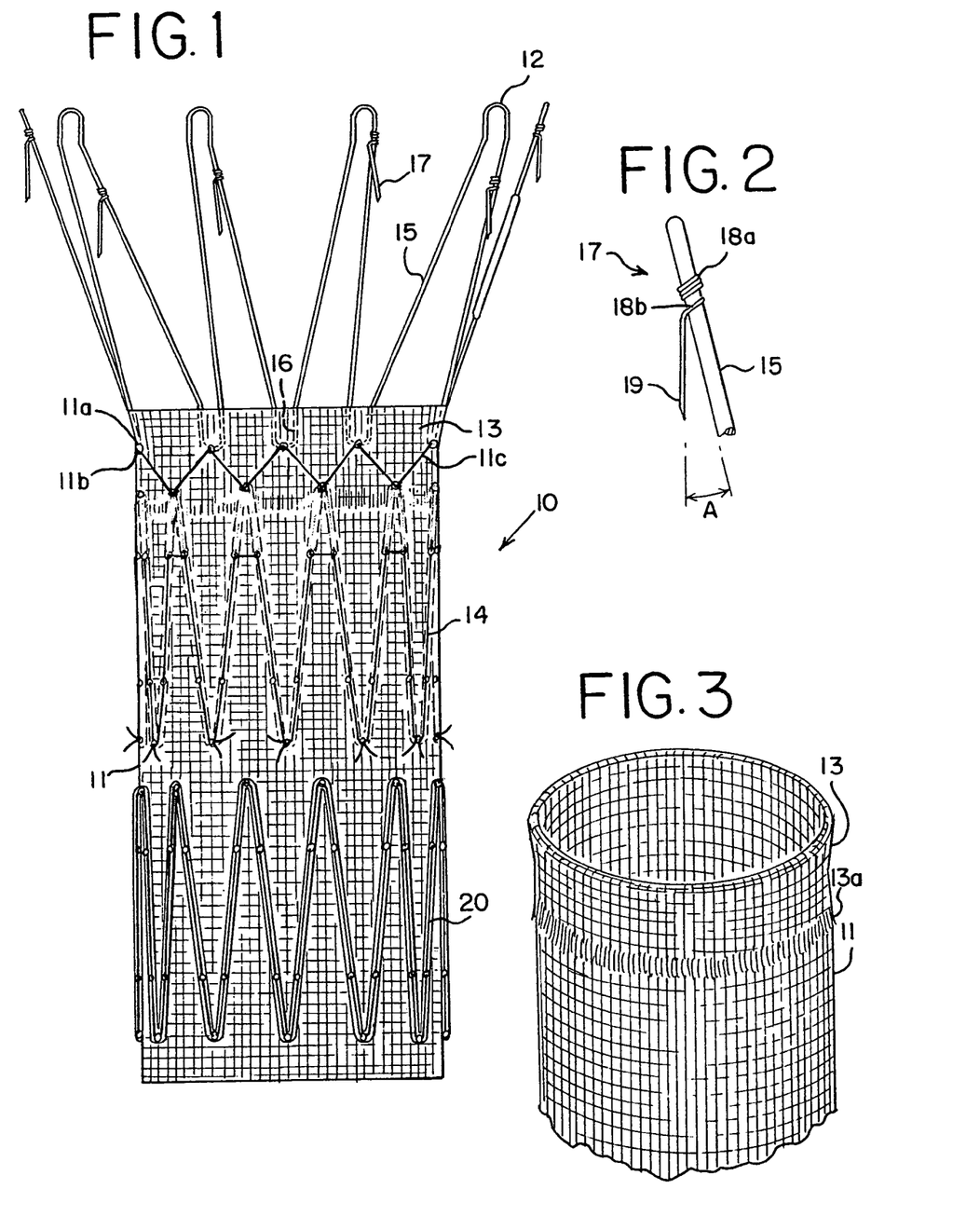
FIG. 1 is an elevational view of a first embodiment.
FIG. 2 is a perspective view of an anchoring barb.
FIG. 3 is a perspective view of an end portion of a graft.

An endoluminal prosthetic device in accordance with the present disclosure is presented in FIG. 1. The device 10 comprises a graft 11 with a cuff 13, made from polyester or other graft material suitable for use in a human body. These materials may include, but are not limited to, polyester, polyurethane, polyethylene, polypropylene, and polytetrafluoroethylene, as well as other fluorinated polymer products. A preferred material is polyester woven in a twill pattern, and available commercially from Vascutek Ltd. of Scotland. Biomaterials may also be used, such as collagen or ECM (extracellular matrix materials). One example is porcine small intestine submucosa (SIS) material, which may be remodeled into repair tissues for the human body.

Device 10 also includes at least one anchoring stent 12 and an internal stent 14. These stents may be in the form of zigzag stents, that is, a continuous chain of struts 15 and joints of apices 16. Zigzag stents known by the trademark Cook-® and stent-grafts for abdominal aortic aneurysm (AAA) repair, made by Cook Incorporated of Bloomington, Ind., are examples of commercial embodiments. Serpentine stents, having curved struts, may also be used.

The preferred embodiment includes an external stent 20. A stent is formed from linear portions or struts 15 and the apex or apices 16 at which the struts meet. In addition, anchoring or exposed stent 12 may include anchors 17, small barbs or hooks that will anchor the stent to the internal wall of a body lumen, such as a wall of an aorta. Anchoring stents are preferably secured to an inside of the graft with sutures. Resiliently compressible, self-expanding stents are preferred in order to seal with the body lumen. PCT Application WO 98/53761, hereby incorporated by reference in its entirety, discloses a number of details concerning stents, stent grafts, and a method for implanting stent grafts into the human body.

The suture may be made of any biocompatible fiber suitable for the application, including but not limited to, monofilament or braided multi-filament material made of polyester, nylon, polyaramid, polypropylene, and polyethylene. Green, braided polyester 4-0 suture material is preferred for attaching internal stents to grafts, while monofilament suture material is preferred for attaching anchoring stents to grafts. The polyester 4-0 suture material is nonabsorbable and has commercial size limits of 0.150 to 0.199 mm (metric size 1.5). Suture materials are commercially available from a number of companies, such as Genzyme Biosurgery, Fall River, Mass. The suture material may be attached to a hollow needle used to thread the suture through the graft, thus attaching the stent to the graft. In making the sutures at the joints described above, suturing may begin at any convenient point.

In the present context, suture means the thread or material that secures the stents to the graft. Suture may also refer to the configuration of this material in a loop, the material securing a portion of a stent to a graft. A suture is made by looping material through the graft and around the stent or an apex of a stent. A knot is then tied, intertwining the ends of the suture in such a way that they will not be easily separated. A suture may have more than one knot. In some cases, or in many cases, an apex of a stent may be secured to the graft by two loops of suture or thread through the graft and also through or around the apex of the stent, and then secured with one knot or more than one knot, in essence tying the ends of the suture. Knots may be locking knots, preferred for apices, or overthreaded knots, preferred along the length of the strut or for other applications. Knots in the stent-graft may include any other useful or desired knots and are not limited to these types.

If the ends of the knot are not cut, the thread or suture may be led by a needle or other mechanical device to the next point on the endoluminal prosthetic device where a suture is desired. The thread or material that joins the first suture to the next suture may be called a running suture, because the thread or suture "runs" between the sutures. A stitch is a single suture. In the present context, every suture is secured with a knot, and where there is a suture, there is at least one loop of thread or material securing a portion of a stent to a graft, and a knot securing the suture. Therefore, whenever a suture other than a running suture is indicated, there is also a knot; the suture and the knot are not shown separately in the drawings.

Sutures for stents are typically not single sutures or single stitches, but typically include two loops through the graft and around the stent or apex that is being joined. The sutures may then be affixed with one or more knots. When the thread penetrates the graft in a two-loop suture, it may be difficult for the needle or other device to penetrate the exact same threads of the graft or the exact same opening with every loop, although this is desired. In the present context, when two stitches share an opening, and there are actually two openings, the sutures are construed as sharing the same opening or penetration if the stitches are within 0 to about 5 threads (warp or weft threads) of each other. Zero is preferable. If a graft is made of a continuous material, such as a biomaterial or collagen, there are no discrete threads in the graft, and the sutures are construed as sharing the same opening or penetration if they are within one suture diameter of each other.

The details of the construction of the endoluminal prosthetic device of FIG. 1 include stents 12 and 14, secured to graft 11 by stitches and knots 11b. The stitches are received in holes or penetrations 11a in graft 11. Stitches 11b in holes 11a secure stents 12, 14 to graft 11. In addition, stitches 11b are linked by running sutures 11c between sutures 11b. The running sutures 11c are formed by letting the thread used for suturing "run" continuously between sutures 11b, rather than cutting the thread after each knot. Each stitch preferably includes at least one knot to secure the stitch in place, so that the stitch will not move, or allow the stent to move, relative to the graft. While each stitch requires two holes or perforations in the graft, the drawings attached hereto may represent each stitch or suture by a single dot or short line. As discussed above, each stitch or suture may in reality represent two stitches or two loops of thread securing a stent to a graft.

The stents may be made from one or more of several materials. These materials include, but are not limited to, stainless steel, titanium, Nitinol, Elgiloy, and shape memory material. These stents are desirably in the form of a zigzag stent, a continuous chain of struts and intersections where the struts meet. As noted above, anchoring stent 12 may have one or more anchors 17, or small barbs, as depicted in greater detail in FIG. 2. Anchor barb 17 on strut 15 of anchoring stent 12 includes securing coils 18a which have a fine pitch, or spacing between coils, and a last coil 18b, which may have a greater pitch than the other coils, ending in anchoring barb 19, which may be oriented at an angle A to a longitudinal axis of an aorta of other body lumen in which the stent-graft is placed. The barb is designed to secure the stent to the wall of the aorta or other blood vessel or body lumen in which the barb is placed, but does not completely penetrate the wall.

The graft, as discussed above, should be suitable for placement inside a person, although these grafts are not limited to uses for humans and may also be used for animals. The graft 11, as depicted in FIG. 3; desirably includes a short cuff 13. This cuff doubles the thickness of the graft for the length of the cuff and thus reinforces the graft in what may be the area of greatest stress. The cuff forms a continuous band of fuzzy, frayed material that is strong and, because of the fraying, encourages tissue ingrowth. A cuff of from about 0.050 inches to about 0.50 inches long may be used.

The embodiment described in FIGS. 1-3 provides excellent retention of stents within or to the graft, while minimizing the number of holes or penetrations through the graft for sutures. In making the sutures at the apices described above, suturing may begin at any convenient point, although it will usually be more convenient to begin suturing the stent that is furthest inward for any graft.

Figure 4:
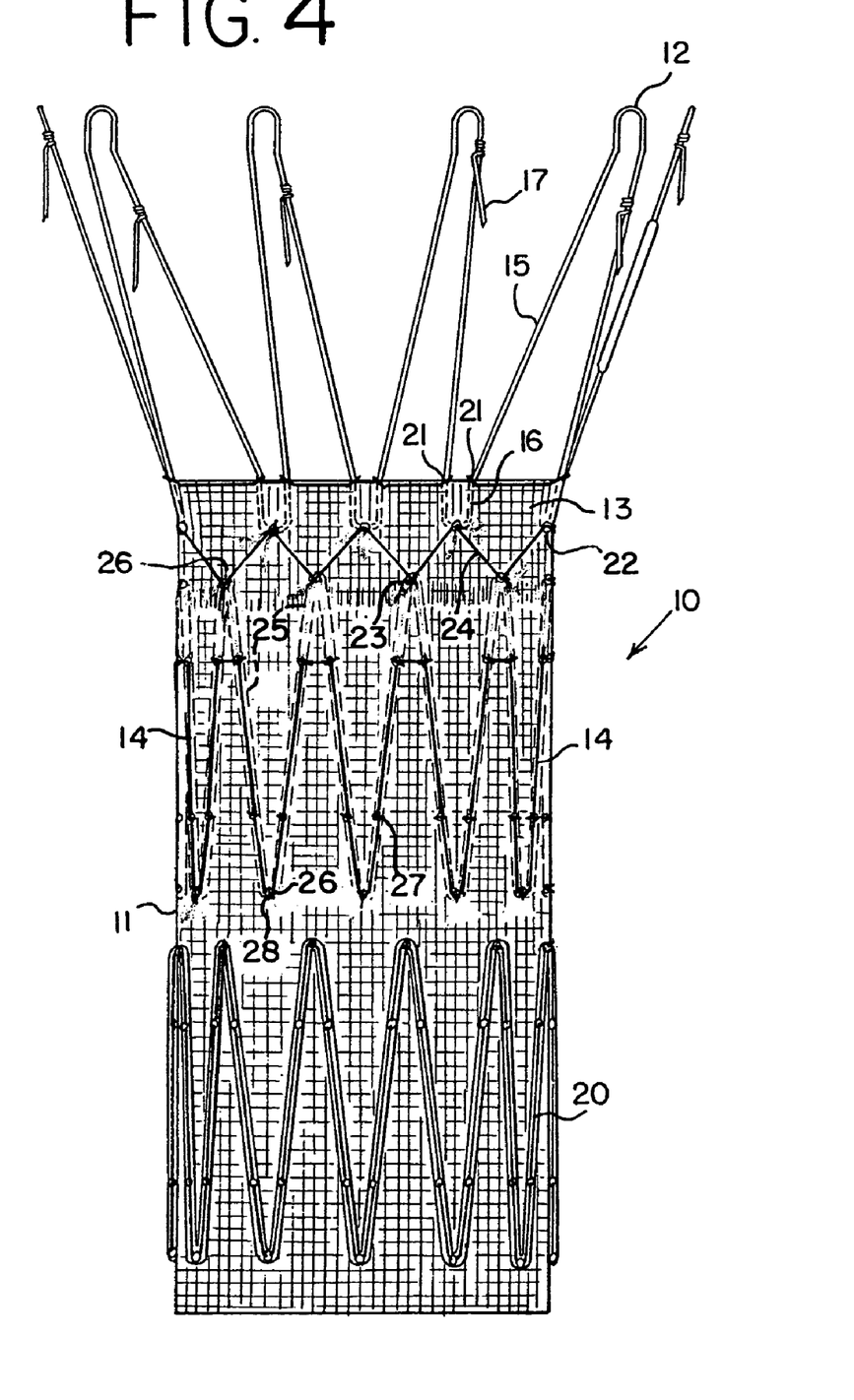
FIG. 4 is a closer view of the first embodiment.

FIG. 4 provides more details of the construction of the embodiment of FIG. 1. Endoluminal prosthetic device 10 includes graft 11, cuff 13, anchoring stent 12 with anchors 17, internal stent 14, and external stent 20. Anchoring stent 12 comprises struts 15 and apices 16 and internal stent 14 comprises struts 25 and apices 26. In this embodiment, each strut 15 of the anchoring stent is secured to the top edge of graft 11 with a stitch 21. Each bottom apex 16 of the anchoring stent is secured to the top edge of graft 11 with a stitch 23. Stitches 23 form a continuous chain with running suture 24 between the bottom apices 16 of anchoring stent 12 and the apices 26 at the top of internal stent 14. Internal stent 14 is also secured to graft 11 with at least one additional stitch 27 on struts 25 and one additional stitch 28 on apices 26 on the bottom of the internal stent. Running suture 24 helps to secure top or anchoring stent 12 together with internal stent 14 to graft 11.

The top edge of graft 11 is preferably formed into a cuff 13 of double thickness in the top half-inch or top quarter-inch, to add strength to the graft where it is most needed. The stitches are preferably made on an outside periphery of the graft. Stitches may also be made on an inside periphery of the graft, but the outside is preferred because it is easier to work on the outside and to leave the "running" portion of the running sutures on the outside of the graft. In addition, it is preferable to leave the inside surfaces of the graft as free from interruptions as possible, in order to avoid thrombi and to encourage flow of body fluids to the greatest extent possible.

Figure 5A:
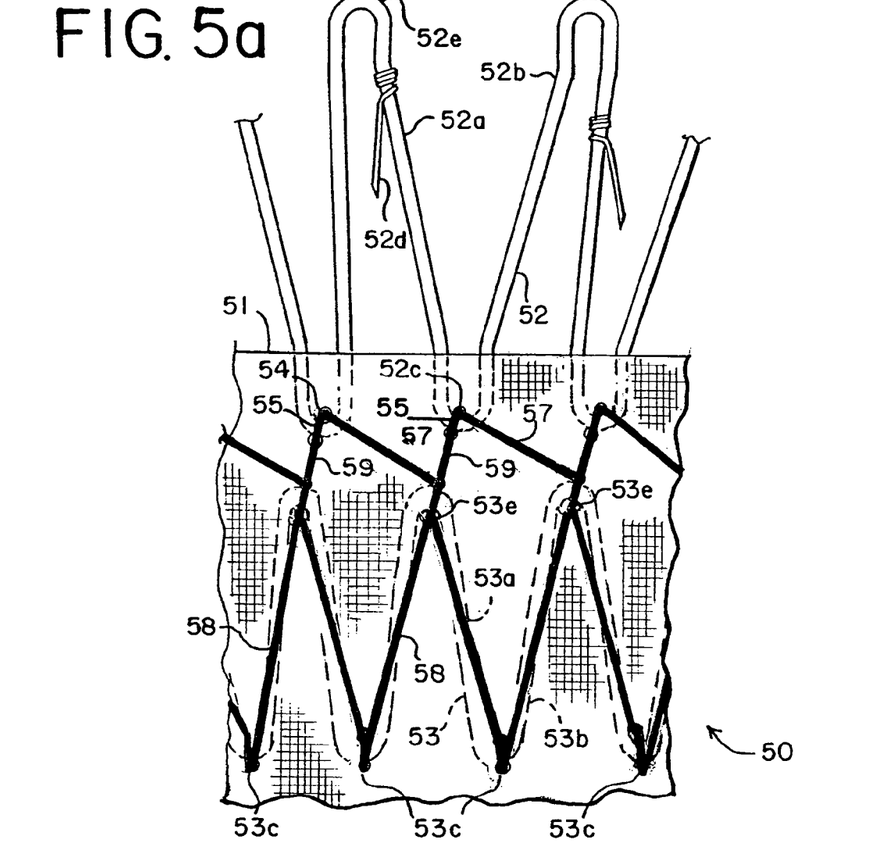
FIG. 5a is an elevational view of a second embodiment.
Figure 5B:
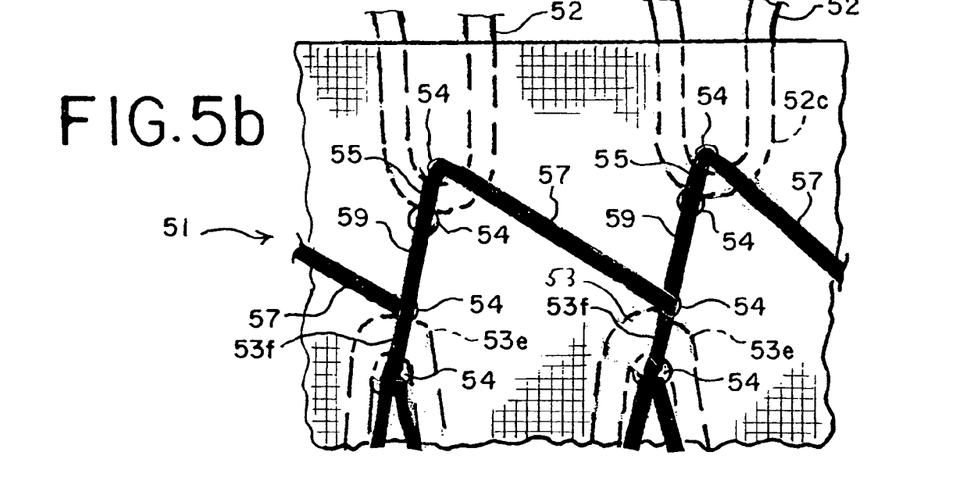

Another embodiment uses a different running suture, as depicted in FIGS. 5a and 5b. In this figure, endoluminal prosthetic device 50 includes a graft 51 having a cylindrical form. The device also includes an anchoring stent 52 for attaching the graft to a body duct or lumen, and an internal stent 53 for sealing the graft to a wall of a body vessel or passageway. Anchoring stent 52 comprises struts 52a, 52b, bottom apices 52c, and top apices 52e. There may also be barbs 52d for anchoring the stent into the body duct or lumen. Internal stent 53 also comprises struts 53a, 53b, bottom apices 53c, and top apices 53e.

The stents are joined to the graft with stitches or sutures 55, depicted as lines in the figures, using holes or penetrations 54 in graft 51. In this embodiment, anchoring stent 52 is joined to the graft with only a single stitch 55 at the bottom apex 52c of each pair of struts 52a, 52b. Internal strut 53 is joined to graft 51 by stitches 53f at bottom and top apices 53c, 53e. The stitches for anchoring stent bottom apex 52c and internal stent top apex 53e are linked by a running suture 59. An additional running suture 57 also extends to one additional top apex 53e. That is, in this embodiment, the running sutures also join the stitches or sutures securing the second-nearest top apex 53e to graft 51. In addition, stitches for internal strut 53 are also linked by a running suture 58 between the stitches. In practice, this structure may be achieved by chain-suturing internal stent 53 to graft 51, and then adding anchoring stent 52 and chain-suturing anchoring stent 52 to the graft in the manner shown with running sutures 57, 59.

It is understood that every joint for a running suture requires at least one stitch, i.e. two openings or penetrations in the graft (whether existing or additional openings), at least a single loop of thread, and at least one knot securing the threads in the area of the penetrations. Adding these additional running sutures strengthens the endoluminal prosthetic device and better secures the stents to the graft. It is preferable to use more than one suture per hole or opening in the graft to achieve a running suture in this manner, rather than to have additional openings.

FIG. 5b is a magnified view of the embodiment of FIG. 5a. Stents 52, 53 are secured to graft 51 using stitches or sutures 53f, 55 and holes or apertures 54 in graft 51. Each suture or stitch requires two apertures or holes. Each top apex 53e of internal stent 53 is near two holes or apertures 54. Apertures 54 and sutures 53f secure internal stent 53 top apices 53e to graft 11. In the same way, apertures 54 and sutures 55 secure bottom apices 52c of anchoring stent 52 to graft 11. Note that each bottom apex 52c is near two apertures 54, for securing by stitches or sutures 53f. In addition, sutures 53f are linked to other sutures by chain-links or running sutures 57, 59. Running sutures 57, 59 link sutures 53f, 55 in a continuous loop or chain on the graft. Since the running sutures are on either the inside or the outside of the graft, they are on a periphery of the graft.

Figure 6:
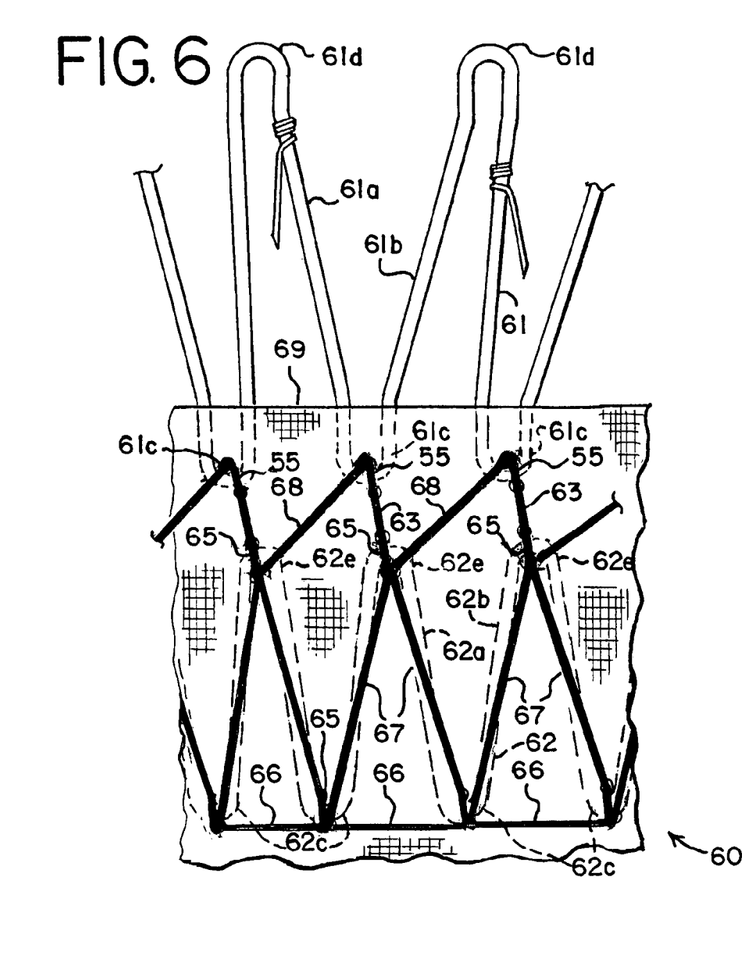
FIG. 6 is an elevational view of a third embodiment.

Another embodiment is depicted in FIG. 6. In this embodiment, endoluminal prosthetic device 60 includes a graft 69, an anchoring stent 61, and an internal stent 62. Anchoring stent 61 includes struts 61a, 61b, and apices 61c, 61d. Internal stent 62 includes struts 62a, 62b, and apices 62c, 62e. Anchoring stent 61 is secured to graft 69 with a stitch or suture 55 at each bottom apex 61c. Internal stent 62 is secured to graft 69 with a stitch or suture 65 at each top apex 62e and each bottom apex 62c. Stitches 55, 65 are linked by running sutures 63, 67, 68. Running sutures 63 link the sutures joining anchoring stent bottom apices 61c to the closest internal stent top apices 62e. Running sutures 67 link sutures 65 securing bottom apices 62c of internal stent 62 with sutures 65 securing top apices 62e of internal stent 62. Running sutures 68 link sutures 65 joining anchoring stent bottom apices 61c to the second-closest internal stent 62 bottom apex 62e. These links provide more stability without extra holes or penetrations in graft 69, because the stitches or sutures share holes in graft 69. Thus, in the embodiment of FIG. 6, there are running sutures 63, 68 between stitches 55 at anchoring stent bottom apices 61c and stitches 65 at internal stent top apices 62e. In addition, there is a running suture 67 linking each stitch 65 at top apices 62e and bottom stitches 65 at bottom apices 62c of internal stent 62. Finally, there is another running suture 66 linking the stitches 65 at the bottom apices 62c of the internal stent.

Figure 7:
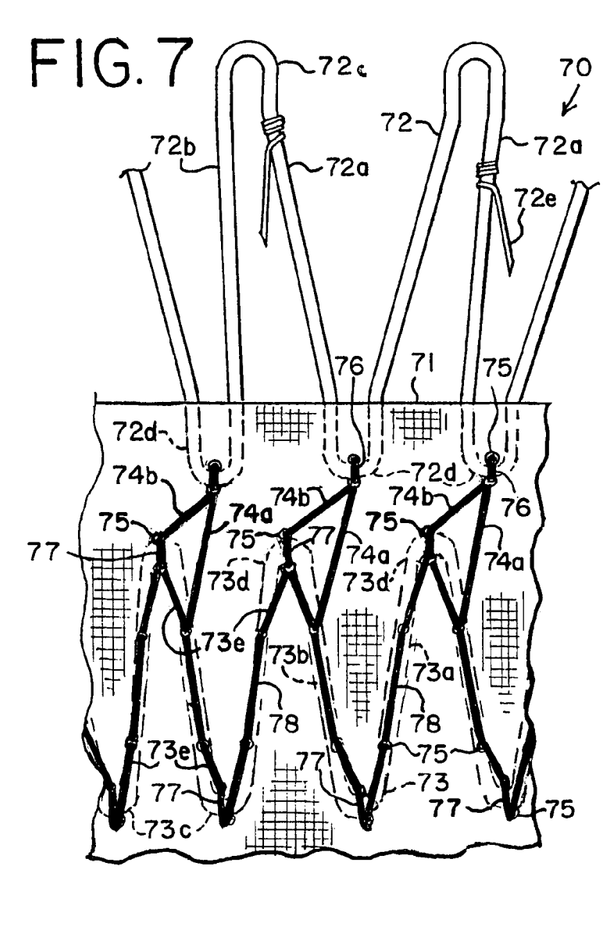
FIG. 7 is an elevational view of a fourth embodiment.

Another embodiment is depicted in FIG. 7, showing another example of a running suture. In this embodiment, endoluminal prosthetic device 70 includes an anchoring stent 72 and an internal stent 73 attached by sutures 76, 77 to graft 71. Sutures are depicted as lines between holes or penetrations 75 in graft 71. Anchoring stent 72 comprises struts 72a, 72b, top apices 72c, bottom apices 72d, and anchoring barbs 72e. Internal stent 73 comprises struts 73a, 73b, bottom apices 73c, and top apices 73d. Anchoring stent 72 is secured to graft 71 by single stitches 76 at top apices 72c. Internal stent 73 is secured to graft 71 by a stitch 77 at each top and bottom apex 73c, 73d, and is also secured by one or two stitches 73e along each strut 73a, 73b. Anchoring stent 72 and internal stent 73 are joined to graft 71 with running sutures 74a, 74b joining sutures 76 at bottom apices 72d, and sutures 77 at top apices 73d. Each strut 73a, 73b on internal stent 73 is secured to the graft with at least one stitch 73e at an intermediate point on the strut, as well as stitches 77 at top and bottom apices 73c, 73d. Running sutures 74a, 74b and 78 link the stitches and strengthen device 70. This arrangement helps to stabilize and anchor the anchoring stent without significantly more penetrations through graft 71, because at least some of the stitches and sutures share the same openings or penetrations in the graft.

Figure 8:
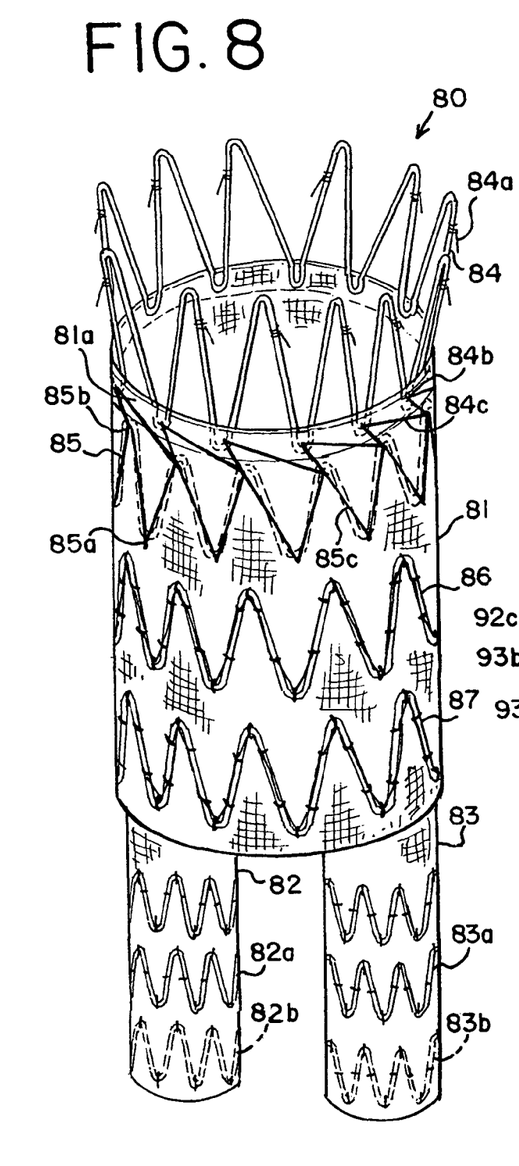
FIG. 8 is a perspective view of a graft with the second embodiment.

An embodiment of the suturing pattern of FIGS. 5a-5b is depicted in the endoluminal prosthetic device of FIG. 8. Aortic stent device 80 comprises a multi-component graft, having an upper portion 81 with a larger diameter, such as for an aorta, and a lower portion having two legs, 82, 83 for first and second iliac arteries. The device includes an anchoring stent 84 with anchoring barbs 84a, the anchoring stent sutured to the upper portion of graft 81 with stitches at the lower apices 84b of the anchoring stent. The upper portion may have a cuff 81a, which may be frayed to promote ingrowth of the graft.

Device 80 also comprises at least one internal stent 85, anchored to upper portion 81 in the manner described for the embodiment of FIG. 5, in which anchoring stent 84 is secured to upper portion 81 with a stitch in each lower apex 84b. Internal stent 85 is anchored to upper portion 81 by a stitch at each top and bottom apex, 85a, 85b. The stitches at junctions 84b, 85a, and 85b form part of a running suture 85c between the stitches at the top and bottom apices of the internal stent, and between the stitches securing top apices 85b and the two nearest bottom apices 84b of anchoring stent 84. Device 80 preferably also includes additional external stents 82a, 83a, and internal stents 82b, 83b as desired. These additional stents may be anchored, such as with barbs as described above. Upper portion 81 may also include additional stents, 86, 87, typically external stents. This embodiment is not limited to an aortic graft, but may be used in other applications, such as a suprarenal graft, where the upper graft is divided for the two renal arteries.

Figure 9:
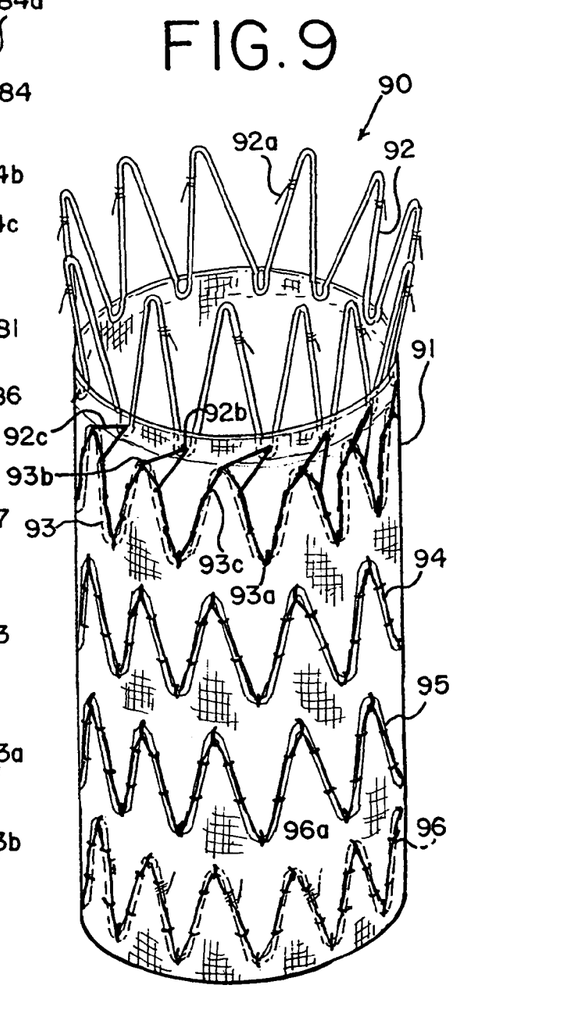
FIG. 9 is a perspective view of an application of the fourth embodiment.

Another embodiment is depicted in FIG. 9. This endoluminal prosthetic device 90 may be used for thoracic insertion. The device includes graft 91 in a cylindrical form, anchoring stent 92 at a distal portion of the device, internal stent 93, external stents 94, 95, and another internal stent 96 at a proximal portion of the device. This device has anchoring stent 92 and internal stent 93 attached in the method depicted in FIG. 7. Anchoring stent 92 is anchored to graft 91 with stitches at each lower apex 92b. Internal stent 93 is anchored to graft 91 at each apex 93a, 93b, and is also tied to graft 91 by at least one stitch on each strut. The stitches on internal stent 93 and the sutures between them form a running suture 93c. In addition, the stitches on anchoring stent 92 and the sutures between them form a running suture 92c between each lower apex 92b and the two closest sutures of internal stent 93. Running sutures 92c, 93c add strength to the bonds between the stents and the graft, thus making for a stronger device.

Figure 10:
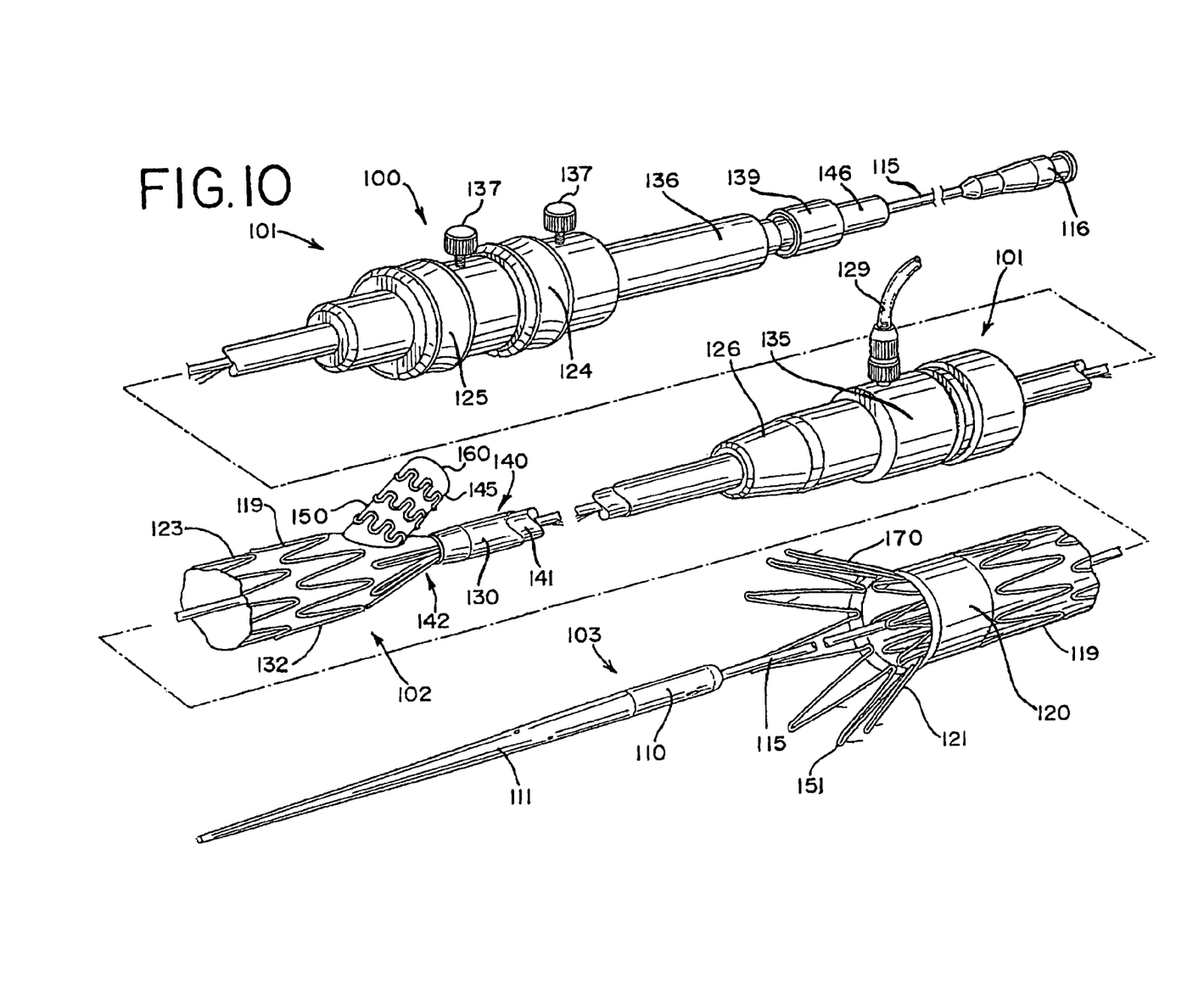
FIG. 10 depicts an apparatus to deploy a prosthesis or prosthetic device.

FIG. 10 shows a self-expanding bifurcated prosthesis 120, a self-expanding tubular prosthesis 150, and an endovascular deployment system 100, also known as an introducer 100, for deploying the prosthesis 120 in a lumen of a patient during a medical procedure. These items are each described in greater detail in PCT application WO98/53761, which was earlier incorporated by reference in its entirety. The terms "proximal" and "proximally" are used for a position or direction towards the patient's heart and the terms "distal" and "distally" are used for a position or direction away from the patient's heart.

The bifurcated prosthesis 120 has a generally inverted Y-shaped configuration. The prosthesis 120 includes a body 123, a shorter leg 160 and a longer leg 132. The bifurcated prosthesis 120 comprises a tubular graft material, such as polyester, with self-expanding stents 119 attached thereto. The self-expanding stents 119 cause the prosthesis 120 to expand following its release from the introducer 100. The prosthesis 120 also includes a self-expanding zigzag stent 121 that extends from its proximal end. The self-expanding zigzag stent 121 has distally extending barbs 151. When it is released from the introducer 100, the self-expanding zigzag stent 121 anchors the barbs 151, and thus the proximal end of the prosthesis 120, to the lumen of the patient.

The self-expanding tubular prosthesis 150 is similar to the bifurcated prosthesis 120, but has a unitary (i.e. non-bifurcated) lumen. The tubular prosthesis 150 also comprises a tubular graft material, such as polyester, having self-expanding stents attached thereto. The tubular prosthesis 150 is configured to connect to the shorter leg 160 of the bifurcated prosthesis 120.

The introducer 100 includes an external manipulation section 101, a distal attachment region 102 and a proximal attachment region 103. The distal attachment region 102 and the proximal attachment region 103 secure the distal and proximal ends of the prosthesis 120, respectively. During the medical procedure to deploy the prosthesis 120, the distal and proximal attachment regions 102 and 103 will travel through the lumen to a desired deployment site. The external manipulation section 101, which is acted upon by a user to manipulate the introducer, remains outside of the patient throughout the procedure.

The proximal attachment region 103 of the introducer 100 includes a cylindrical sleeve 110. The cylindrical sleeve 110 has a long tapered flexible extension 111 extending from its proximal end. The flexible extension 111 has an internal longitudinal aperture (not shown). This longitudinal aperture facilitates advancement of the tapered flexible extension 111 along an insertion wire (not shown). The longitudinal aperture also provides a channel for the introduction of medical reagents. For example, it may be desirable to supply a contrast agent to allow angiography to be performed during placement and deployment phases of the medical procedure.

A thin walled metal tube 115 is fastened to the extension 111. The thin walled metal tube 115 is flexible so that the introducer 100 can be advanced along a relatively tortuous vessel, such as a femoral artery, and so that the distal attachment region 102 can be longitudinally and rotationally manipulated. The thin walled metal tube 115 extends through the introducer 100 to the manipulation section 101, terminating at a connection means 116.

The connection means 116 is adapted to accept a syringe to facilitate the introduction of reagents into the thin walled metal tube 115. The thin walled metal tube 115 is in fluid communication with the apertures 112 of the flexible extension 111. Therefore, reagents introduced into connection means 116 will flow to and emanate from the apertures 112.

A plastic tube 141 is coaxial with and radially outside of the thin walled metal tube 115. The plastic tube 141 is "thick walled"—its wall is preferably several times thicker than that of the thin walled metal tube 115. A sheath 130 is coaxial with and radially outside of the plastic tube 141. The thick walled plastic tube 141 and the sheath 130 extend distally to the manipulation region 101.

During the placement phase of the medical procedure, the prosthesis 120 is retained in a compressed condition by the sheath 130. The sheath 130 extends distally to a gripping and haemostatic sealing means 135 of the external manipulation section 101. During assembly of the introducer 100, the sheath 130 is advanced over the cylindrical sleeve 110 of the proximal attachment region 103 while the prosthesis 120 is held in a compressed state by an external force. A distal attachment (retention) section 140 (inside sheath 130 and not visible in this view) is coupled to the thick walled plastic tube 141. The distal attachment section 140 retains a distal end 142 of the prosthesis 120 during the procedure. Likewise, the cylindrical sleeve 110 retains the self-expanding zigzag stent 121.

The distal end 142 of the prosthesis 120 is retained by the distal attachment section 140. The distal end 142 of the prosthesis 120 has a loop (not shown) through which a distal trigger wire (not shown) extends. The distal trigger wire extends through an aperture (not shown) in the distal attachment section 140 into an annular region between the thin walled tube 115 and the thick walled tube 141. The distal trigger wire extends through the annular space to the manipulation region 101. The distal trigger wire exits the annular space at a distal wire release mechanism 125.

The external manipulation section 101 includes a haemostatic sealing means 135. The haemostatic sealing means 135 includes a haemostatic seal (not shown) and a side tube 129. The haemostatic sealing means 135 also includes a clamping collar (not shown) that clamps the sheath 130 to the haemostatic seal, and a silicone seal ring (not shown) that forms a haemostatic seal around the thick walled plastic tube 141. The side tube 129 facilitates the introduction of medical reagents between the thick walled tube 141 and the sheath 130.

A proximal portion of the external manipulation section 101 includes a release wire actuation section that has a body 136. The body 136 is mounted onto the thick walled plastic tube 141. The thin walled tube 115 passes through the body 136. The distal wire release mechanism 125 and the proximal wire release mechanism 124 are mounted for slidable movement onto the body 136.

The positioning of the proximal and distal wire release mechanisms 124 and 125 is such that the proximal wire release mechanism 124 must be moved before the distal wire release mechanism 125 can be moved. Therefore, the distal end 142 of the prosthesis 120 cannot be released until the self-expanding zigzag stent 121 has been released, and the barbs 151 have been anchored to the lumen. Clamping screws 137 prevent inadvertent early release of the prosthesis 120. A haemostatic seal (not shown) is included so that the release wires can extend out through the body 136 without unnecessary blood loss during the medical procedure.

A distal portion of the external manipulation section 101 includes a pin vise 139. The pin vise 139 is mounted onto the distal end of the body 136. The pin vise 139 has a screw cap 146. When screwed in, vise jaws (not shown) of the pin vise 139 clamp against or engage the thin walled metal tube 115. When the vise jaws are engaged, the thin walled tube 115 can only move with the body 136, and hence the thin walled tube 115 can only move with the thick walled tube 141. With the screw cap 146 tightened, the entire assembly can be moved together as one piece.

A second introducer may be used to introduce the tubular prosthesis 150. This second introducer may be based on the same principles as the introducer 100 described above, but less complex. For example, the second introducer may include a complex sheath for containing the tubular prosthesis 150 in a compressed state, so that it can be introduced into a targeted anatomy and then released to either self-expand or be actively expanded with a balloon.

The second introducer may also be adapted so that it can introduce the tubular prosthesis 150 by passing it through one ostium in the bifurcated prosthesis 120 and partially out of another ostium until the terminus of the tubular prosthesis 150 that is closest to the external end of the second introducer is properly positioned. At that point, the tubular prosthesis 150 can be released from the second introducer.

Deployment

Prosthetic modules are preferably deployed seriatim. The intermodular connection between the tubular prosthesis 150 and the bifurcated prosthesis 120 is formed in situ. First the bifurcated prosthesis 120 is deployed, and then the tubular prosthesis 150 is deployed. For example, a bifurcated aortic prosthesis 120, as described in WO98/53761, incorporated above by reference in its entirety, can be deployed into the abdominal aorta. The bifurcated prosthesis 120 has a generally inverted Y-shaped configuration having a body portion 123, a shorter leg 160 and a longer leg 132. The body of the prosthesis is constructed from a tubular woven polyester. At the proximal end of the prosthesis 120 is a self-expanding stent 121 which extends beyond the end of the prosthesis and has distally extending barbs 151. The shorter leg 160 and the longer leg 132 have internal projections extending from their distal termini.

This bifurcated prosthesis 120 can be deployed in any method known in the art, preferably the method described in WO98/53761 in which the device is inserted by an introducer via a surgical cut-down into a femoral artery, and then advanced into the desired position over a stiff wire guide using endoluminal interventional techniques. For example, a guide wire (not shown) is first introduced into a femoral artery of the patient and advanced until its tip is beyond the desired deployment region of the prosthesis 120. At this stage, the introducer assembly 100 is fully assembled, and ready for introduction into the patient. The prosthesis 120 is retained at one end by the cylindrical sleeve 110 and the other by the distal attachment sections 140, and compressed by the sheath 130. If an aortic aneurysm is to be repaired, the introducer assembly 100 can be inserted through a femoral artery over the guide wire, and positioned by radiographic techniques, which are not discussed here.

Once the introducer assembly 100 is in the desired deployment position, the sheath 130 is withdrawn to just proximal of the distal attachment section 140. This action releases the middle portion of the prosthesis 120 so that it can expand radially. Consequently, the prosthesis 120 can still be rotated or lengthened or shortened for accurate positioning. The proximal self-expanding stent 121, however, is still retained within the cylindrical sleeve 110. Also, the distal end 142 of the prosthesis 120 is still retained within the external sheath 130.

Next, the pin vise 139 is released to allow small movements of the thin walled tube 115 with respect to the thick walled tube 141. These movements allow the prosthesis 120 to be lengthened or shortened or rotated or compressed for accurate placement in the desired location within the lumen. X-ray opaque markers (not shown) may be placed along the prosthesis 120 to assist with placement of the prosthesis.

When the proximal end of the prosthesis 120 is in place, the proximal trigger wire is withdrawn by distal movement of the proximal wire release mechanism 124. The proximal wire release mechanism 124 and the proximal trigger wire can be completely removed by passing the proximal wire release mechanism 124 over the pin vise 139, the screw cap 146, and the connection means 116.

Next, the screw cap 146 of the pin vise 139 is then loosened. After this loosening, the thin walled tube 115 can be pushed in a proximal direction to move the cylindrical sleeve 110 in a proximal direction. When the cylindrical sleeve 110 no longer surrounds the self-expanding stent 121, the self-expanding stent 121 expands. When the self-expanding stent 121 expands, the barbs 151 grip the walls of the lumen to hold the proximal end of the prosthesis 120 in place. From this stage on, the proximal end of the prosthesis 120 cannot be moved again.

Once the proximal end of the prosthesis 120 is anchored, the external sheath 130 is withdrawn distally of the distal attachment section 140. This withdrawal allows the contralateral limb 160 and the longer leg 132 of the prosthesis 120 to expand. At this point, the distal end 142 of the prosthesis 120 may still be moved. Such positioning of the prosthesis 120 may ensure that the shorter leg 160 extends in the direction of a contralateral artery.

After the shorter leg 160 extends in the direction of the contra-iliac artery, the tubular prosthesis 150 is deployed. The tubular prosthesis 150 is deployed such that it forms a connection with the shorter leg 160 and extends from the shorter leg 160 into the contralateral artery.

There are many ways of practicing the invention. For instance, rather than having a continuous chain of running sutures on an outside periphery of the graft, it is possible to strengthen the attachment of the stent by more than one running suture, such as a running suture that links 4 or 5 stitches or apices of a stent to the graft. Other equivalents may include shorter links that join both an anchoring stent and a second stent to the graft, the shorter links comprising as few as two or three apices.

Some anchoring stents are referred to as "top" stents, but an anchoring or top or "bare" stent need not be vertically on top of the graft or another stent. Depending on the application, an anchoring stent may be vertically higher or lower than a neighboring stent, or an anchoring stent may be placed horizontally side by side another stent in a stent-graft or other endoluminal prosthetic device. The embodiments depicted herein include anchoring stents, but embodiments of the invention in which two or more stents are joined in a graft with a running stitch are not limited to anchoring stents. Embodiments may include other stent combinations, such as two internal stents, two external stents, or an internal and an external stent. All such devices and methods may be equivalent to the inventions described above and claimed in the claims attached hereto.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of even one of rudimentary skills in this area, in view of the present disclosure.

Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described herein with reference to the illustrative embodiments. Unless otherwise indicates, all ordinary words and terms used herein shall take their customary meaning as defined in the New Shorter Oxford English Dictionary, 1993 edition. All technical terms not defined herein shall take on their customary meaning as established by the appropriate technical discipline utilized by those normally skilled in that particular art area. All medical terms not otherwise defined shall take their meaning as defined by Stedman's Medical Dictionary, 27th edition.

What is claimed is:

1. An endoluminal prosthetic device, comprising:
  a graft comprising a bio-compatible material and at least one lumen extending longitudinally therein;
  a first stent comprising a plurality of struts and apices between the struts, wherein at least one apex in the first stent is secured to the graft by looping a thread around and at the apex and through the graft material forming a first knotted stitch, and wherein the first knotted stitch prevents the at least one apex in the first stent from moving relative to the graft; and
  a second stent comprising a plurality of struts and apices between the struts, wherein at least one apex in the second stent is secured to the graft by looping the thread around and at the apex and through the graft material forming a second knotted stitch, wherein the second knotted stitch is formed by the same thread forming the first knotted stitch, and wherein the second knotted stitch prevents the at least one apex in the second stent from moving relative to the graft,
  wherein the thread forms a running suture linking the first knotted stitch of the first stent and the second knotted stitch of the second stent, wherein the running suture extends at least partially in a longitudinal direction from the first knotted stitch to the second knotted stitch; and
  wherein the running suture strengthens the endoluminal prosthetic device by adding strength to bonds between the first stent, the second stent, and the graft.

2. The endoluminal prosthetic device of claim 1, wherein the first stent is an anchoring stent and the second stent is an internal stent.

3. The endoluminal prosthetic device of claim 1, wherein the graft is made of material selected from the group consisting of polyester, polyurethane, polyethylene, polypropylene and polytetrafluoroethylene.

4. The endoluminal prosthetic device of claim 1, wherein the suture further comprises monofilament or braided multifilament material selected from the group consisting of polyester, nylon, polyaramid, polypropylene, and polyethylene.

5. The endoluminal prosthetic device of claim 1, wherein the stents comprise material selected from the group consisting of stainless steel, titanium, and shape memory material.

6. The endoluminal prosthetic device of claim 1 further comprising a cuff on the graft.

7. The endoluminal prosthetic device of claim 1, wherein the graft incorporates biomaterial selected from the group consisting of collagen, extracellular matrix material, and small intestine submucosa (SIS).

8. The endoluminal prosthetic device of claim 1, wherein at least one of the first stent and the second stent are secured by an additional stitch on at least two of the struts.

9. The endoluminal prosthetic device of claim 1, wherein the first stent is an anchoring stent and wherein at least one of the struts further comprises a barb for retaining the endoluminal prosthetic device in place.

10. The endoluminal prosthetic device of claim 1, further comprising additional stitches linked to the running suture.

11. The endoluminal prosthetic device of claim 1, wherein the amount of travel of the running suture between the first stitch and the second stitch in the longitudinal direction is less than the amount of travel in the circumferential direction.

12. A method of forming an endoluminal prosthetic device, the method comprising:
  providing a graft comprising a bio-compatible material and at least one lumen extending longitudinally therein;
  providing the device with a plurality of stitches;
  joining a first stent to the graft, the first stent comprising a plurality of struts and apices between the struts, by at least one first stitch of the plurality of stitches,
  wherein the at least one first stitch is formed by a thread looping around and at an apex of the plurality of apices and through the graft material thereby forming a first knotted stitch, and wherein each first stitch prevents one of the plurality of apices in the first stent from moving relative to the graft;
  running the thread to a second stent at least partially in a longitudinal direction;
  joining the second stent to the graft, the second stent comprising a plurality of struts and apices between the struts, by at least one second stitch of the plurality of stitches, wherein the at least one second stitch is formed by the thread a looping around and at an apex of the plurality of apices and through the graft material thereby forming a second knotted stitch, and wherein each second stitch prevents one of the plurality of apices in the second stent from moving relative to the graft; and
  forming a running suture between the at least one first stitch and the at least one second stitch, wherein the running suture strengthens the endoluminal prosthetic device by adding strength to bonds between the first stent, the second stent, and the graft.

13. The method of claim 12, wherein the first stent is an anchoring stent and further comprising forming a barb on at least one strut of the anchoring stent.

14. The method of claim 12, further comprising folding the graft to form a cuff before the step of joining the first stent.

15. The method of claim 12, further comprising forming at least one penetration in the graft before the steps of joining.

16. The method of claim 12, further comprising linking at least one additional stitch to the running suture.

17. The method of claim 12, further comprising linking at least one additional stitch to the running suture, wherein at least two stitches share an opening in the graft.

18. The method of claim 12, further comprising linking at least one additional stitch to the running suture, wherein at least two stitches are within one suture diameter of each other.

19. An endoluminal prosthetic device, comprising:
- a graft comprising a bio-compatible material and at least one lumen extending longitudinally therein;
- a plurality of stitches;
- a first stent comprising a plurality of struts and apices between the struts, wherein a first apex in the first stent is secured to the graft by looping a thread around the first apex and through the graft material forming a first knotted stitch, and wherein the first knotted stitch prevents the first apex in the first stent from moving relative to the graft;
- a second stent comprising a plurality of struts and apices between the struts, wherein a first apex in the second stent is secured to the graft by looping the thread around the first apex of the second stent and through the graft material forming a second knotted stitch, and wherein the second knotted stitch prevents the first apex in the second stent from moving relative to the graft;
- a second apex in the first stent is secured to the graft by looping the thread around the second apex of the first stent and through the graft material forming a third knotted stitch, wherein the third knotted stitch prevents the second apex in the first stent from moving relative to the graft;
- wherein the device further comprises a running suture linking together the first knotted stitch to the second knotted and the second knotted stitch to the third knotted stitch, wherein the running suture is formed of the thread that also forms the first, second, and third knotted stitches; and
- wherein the running suture strengthens the endoluminal prosthetic device by adding strength to bonds between the first stent, the second stent, and the graft.

20. The endoluminal prosthetic device of claim 19, wherein the amount of travel of the running suture between the first knotted stitch and the second knotted stitch in the longitudinal direction is less than the amount of travel between in the circumferential direction.

* * * * *

UNITED STATES PATENT AND TRADEMARK OFFICE
CERTIFICATE OF CORRECTION

PATENT NO. : 8,348,988 B2  
APPLICATION NO. : 11/037792  
DATED : January 8, 2013  
INVENTOR(S) : Ashvin Lad et al.

Page 1 of 1

It is certified that error appears in the above-identified patent and that said Letters Patent is hereby corrected as shown below:

In the Claims

In column 14, claim 19, line 8, after "to the second knotted" insert --stitch--.

Signed and Sealed this  
Twenty-first Day of October, 2014

Michelle K. Lee  
*Deputy Director of the United States Patent and Trademark Office*